US00PP31158P3

(12) United States Plant Patent
Wain

(10) Patent No.: US PP31,158 P3
(45) Date of Patent: Dec. 3, 2019

(54) ***CHRYSANTHEMUM* PLANT NAMED 'FICHRYRAINSUN'**

(50) Latin Name: ***Chrysanthemum* X *morifolium***
Varietal Denomination: Fichryrainsun

(71) Applicant: DUMMEN GROUP B.V., De Lier (NL)

(72) Inventor: Peter Wain, Locks Heath (GB)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/732,516

(22) Filed: Nov. 21, 2017

(65) Prior Publication Data

US 2018/0146603 P1 May 24, 2018

Related U.S. Application Data

(60) Provisional application No. 62/497,574, filed on Nov. 22, 2016.

(51) Int. Cl.
*A01H 5/02* (2018.01)
*A01H 6/14* (2018.01)

(52) U.S. Cl.
USPC ..... Plt./286
CPC ..... *A01H 6/1424* (2018.05); *A01H 5/02* (2013.01)

(58) Field of Classification Search
USPC ..... Plt./286, 298
CPC ..... A01H 5/0255; A01H 5/02; A01H 5/00; A01H 6/1424; A01H 6/14
See application file for complete search history.

*Primary Examiner* — June Hwu
(74) *Attorney, Agent, or Firm* — C. A. Whealy

(57) ABSTRACT

A new and distinct cultivar of *Chrysanthemum* plant named 'Fichryrainsun', characterized by its upright to outwardly spreading and uniformly mounded plant habit; moderately vigorous growth habit; freely branching habit; dense and full plant form; uniform and freely flowering habit; large semi-decorative type inflorescences with red and yellow bi-colored ray florets; response time about 51 days under controlled photoperiodic treatments; and good postproduction longevity.

1 Drawing Sheet

Botanical designation: *Chrysanthemum* X *morifolium*.
Cultivar denomination: 'FICHRYRAINSUN'.

BACKGROUND OF THE INVENTION

The present invention relates to a new and distinct *Chrysanthemum* plant, botanically known as *Chrysanthemum* X *morifolium*, commercially grown as a garden *Chrysanthemum* plant, referred to as code number 65712 in U.S. Provisional Patent Application Ser. No. 62/497,574 and hereinafter referred to by the name 'Fichryrainsun'.

The new *Chrysanthemum* plant is a product of a planned breeding program conducted by the Inventor in Fareham, Hampshire, United Kingdom. The objective of the breeding program is to create new potted *Chrysanthemum* plants with numerous attractive inflorescences.

The new *Chrysanthemum* plant originated from a cross-pollination made in January, 2013 by the Inventor in Fareham, Hampshire, United Kingdom of a proprietary selection of *Chrysanthemum* X *morifolium* identified as code number 807341, not patented, as the female, or seed, parent with a proprietary selection of *Chrysanthemum* X *morifolium* identified as code number 87333, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2013.

Asexual reproduction of the new *Chrysanthemum* plant by terminal vegetative cuttings was first conducted in Fareham, Hampshire, United Kingdom in December, 2013. Asexual reproduction by terminal vegetative cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Fichryrainsun'. These characteristics in combination distinguish 'Fichryrainsun' as a new and distinct *Chrysanthemum* plant:

1. Upright to outwardly spreading and uniformly mounded plant habit.
2. Moderately vigorous growth habit.
3. Freely branching habit; dense and full plant form.
4. Uniform and freely flowering habit.
5. Large semi-decorative type inflorescences with red and yellow bi-colored ray florets.
6. Response time about 51 days under controlled photoperiodic treatments.
7. Good postproduction longevity.

Plants of the new *Chrysanthemum* can be compared to plants of the female parent selection. Plants of the new *Chrysanthemum* differ primarily from plants of the female parent selection in the following characteristics:

1. Plants of the new *Chrysanthemum* flower about three days later than plants of the female parent selection.

2. Plants of the new *Chrysanthemum* and the female parent selection differ in ray floret color as plants of the female parent selection have inflorescences with pink and white bi-colored ray florets.

Plants of the new *Chrysanthemum* can be compared to plants of the male parent selection. Plants of the new *Chrysanthemum* differ primarily from plants of the male parent selection in the following characteristics:

1. Plants of the new *Chrysanthemum* flower about five days later than plants of the male parent selection.
2. Plants of the new *Chrysanthemum* and the male parent selection differ in ray floret color as plants of the male parent selection have inflorescences with solid red-colored ray florets.

Plants of the new *Chrysanthemum* can be compared to plants of *Chrysanthemum* X *morifolium* 'Breeze Cardinal', not patented. In side-by-side comparisons, plants of the new *Chrysanthemum* differ primarily from plants of 'Breeze Cardinal' in the following characteristics:

1. Plants of the new *Chrysanthemum* flower about five days later than plants of 'Breeze Cardinal'.
2. Plants of the new *Chrysanthemum* and 'Breeze Cardinal' differ in ray floret color as plants of 'Breeze Cardinal' have inflorescences with solid red-colored ray florets.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant. The photograph is a top perspective view of a typical flowering plant of 'Fichryrainsun' grown in a 14-cm container.

DETAILED BOTANICAL DESCRIPTION

The aforementioned photograph and following observations and measurements describe plants grown during the spring in 14-cm containers in a glass-covered greenhouse in Fareham, Hampshire, United Kingdom and under cultural practices typical of commercial garden *Chrysanthemum* production. During the production of the plants, day and night temperatures ranged from 17° C. to 21° C. and light levels averaged 6,000 lux. Plants were grown under long day/short night conditions for about two weeks and then grown under short day/long night conditions to induce inflorescence initiation and development. Plants were nine weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum* X *morifolium* 'Fichryrainsun'.

Parentage:

*Female, or seed, parent.*—Proprietary selection of *Chrysanthemum* X *morifolium* identified as code number 807341, not patented.

*Male, or pollen, parent.*—Proprietary selection of *Chrysanthemum* X *morifolium* identified as code number 87333, not patented.

Propagation:

*Type.*—Terminal vegetative cuttings.

*Time to initiate roots, summer.*—About ten days at temperatures about 21° C.

*Time to initiate roots, winter.*—About two weeks at temperatures about 21° C.

*Time to produce a rooted young plant, summer.*—About three weeks at temperatures about 21° C.

*Time to produce a rooted young plant, winter.*—About four weeks at temperatures about 21° C.

*Root description.*—Fine, fibrous; typically light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Herbaceous semi-decorative type potted *Chrysanthemum*; stems upright to outwardly spreading giving a uniformly mounded appearance to the plant; numerous lateral branches and relatively short internodes, dense and full plant form; moderately vigorous growth habit.

*Plant height.*—About 19 cm.

*Plant width.*—About 34 cm.

*Branching habit.*—Freely branching habit; about four primary lateral branches develop after removal of terminal apex (pinching).

*Lateral branches.*—Length: About 12 cm. Diameter: About 4 mm. Internode length: About 1.3 cm. Strength: Strong. Aspect: About 60° from vertical and then bending upwardly. Texture: Fine pubescence. Color: Close to 146B.

Leaf description:

*Arrangement.*—Alternate, simple.

*Length.*—About 6.2 cm.

*Width.*—About 4.2 cm.

*Shape.*—Palmately-lobed; roughly ovate with three to five lobes.

*Apex.*—Broadly acuminate.

*Base.*—Attenuate.

*Margin.*—Slightly dentate and palmately lobed; sinuses between lateral lobes mostly divergent.

*Texture, upper and lower surfaces.*—Fine pubescence; slightly rough; veins prominent on lower surface.

*Color.*—Developing leaves, upper surface: Close to N137A. Developing leaves, lower surface: Close to 137C. Fully expanded leaves, upper surface: Close to N137A; venation, close to 146B. Fully expanded leaves, lower surface: Close to 147B; venation, close to 146B.

*Petioles.*—Length: About 1.5 cm. Diameter: About 3 mm. Texture, upper and lower surfaces: Fine pubescence; slightly rough. Color, upper and lower surfaces: Close to 146B.

Inflorescence description:

*Form and flowering habit.*—Semi-decorative type inflorescence form with ligulate-shaped ray florets; inflorescences borne on terminals above and beyond the foliar plane; disc and ray florets arranged acropetally on a capitulum; freely flowering habit with about 24 inflorescences developing per plant during the flowering season.

*Fragrance.*—Mildly fragrant; pungent, herbaceous.

*Flowering response.*—Plants flower uniformly about 51 days after starting short day/long night photoperiodic treatments.

*Inflorescence longevity.*—Good postproduction longevity; inflorescences maintain good color and substance for about two to three weeks on the plant; inflorescences persistent.

*Inflorescence buds.*—Height: About 5 mm. Diameter: About 8 mm. Shape: Oblate. Color: Close to 138A.

*Inflorescence diameter.*—Large, about 8 cm.

*Inflorescence height.*—About 2.8 cm.

*Disc diameter.*—About 1.5 cm.

*Receptacles.*—Height: About 5 mm. Diameter: About 6 mm. Shape: Conical. Color: Close to 145B.

*Ray florets.*—Number of ray florets per inflorescence: About 25 arranged in about two whorls. Orientation: Initially upright, then about 45° from vertical. Length: About 3 cm. Width: About 9 mm. Shape: Ligulate. Apex: Mammillate. Base: Fused into a short tube. Margin: Entire. Texture, upper and lower surfaces: Smooth, glabrous; double-keeled. Color: When opening, upper surface: Center and distally, close to 187C and towards the base, 14B. When opening, lower surface: Center and distally, close to 187C and towards the base, 13B. Fully opened, upper surface: Center and distally, close to 53A and towards the base, 23B; with development, colors becoming closer to 187C and 14B. Fully opened, lower surface: Close to 183C and 7B; with development, colors becoming closer to 187C and 13B.

*Disc florets.*—Number of disc florets per inflorescence: About 160 massed at the center of the receptacle. Length: About 6 mm. Diameter: About 1 mm. Shape: Tubular, elongated; apices, acute. Texture, inner and outer surfaces: Smooth, glabrous. Color, when opening and fully opened: Apex: Close to 9A. Midsection: Close to 145A. Base: Close to 157D.

*Phyllaries.*—Number of phyllaries per inflorescence: About 25 arranged in about two whorls. Length: About 9 mm. Width: About 3 mm. Shape: Lanceolate. Apex: Obtuse. Base: Obtuse. Margin: Entire. Texture, upper surface: Smooth, glabrous; waxy. Texture, lower surface: Fine pubescence; waxy. Color, upper and lower surfaces: Close to 137C.

*Peduncles.*—Length, terminal peduncle: About 2 cm. Diameter, terminal peduncle: About 2 mm. Angle: Erect to about 20° from vertical. Strength: Moderately strong. Texture: Pubescent. Color: Close to 138A.

*Reproductive organs.*—Androecium: None observed. Gynoecium: Present only on ray florets. Pistil length: About 6 mm. Stigma shape: Bi-parted. Stigma color: Close to 7A. Style length: About 0.4 mm. Style color: Close to 145B. Ovary color: Close to 1D.

*Seeds and fruits.*—Seed and fruit production has not been observed on plants of the new *Chrysanthemum* to date.

Disease & pest resistance: Resistance to pathogens and pests common to *Chrysanthemum* plants has not been observed on plants of the new *Chrysanthemum* to date.

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Fichryrainsun' as illustrated and described.

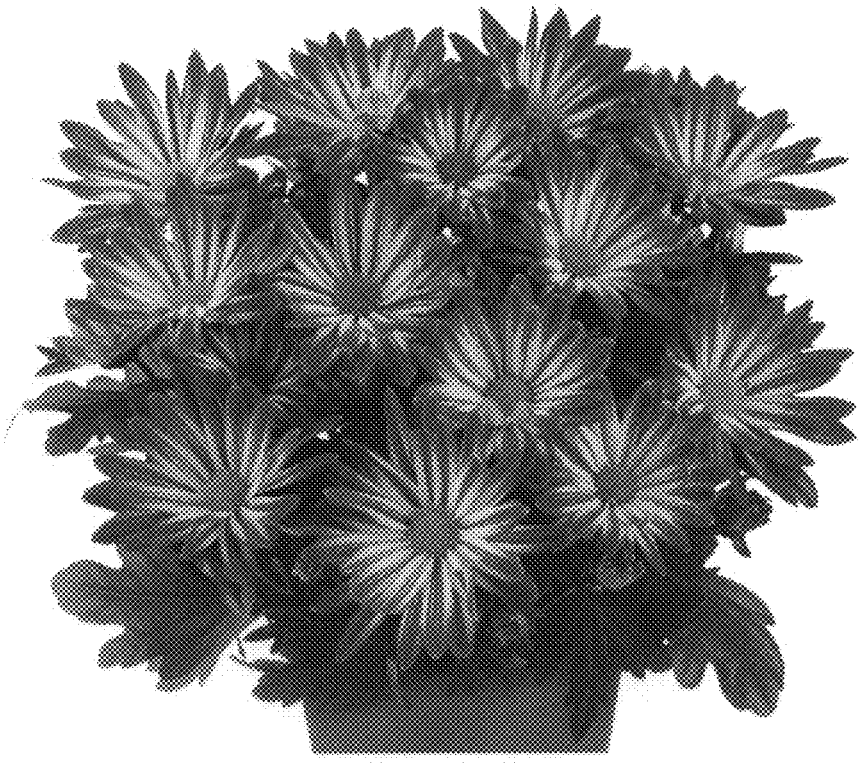

* * * * *